United States Patent [19]

Masereel et al.

[11] Patent Number: 5,391,559
[45] Date of Patent: Feb. 21, 1995

[54] NEW PYRIDYLSULPHONYLUREA COMPOUND

[75] Inventors: Bernard Masereel, Libin; Bernard Pirotte, Oupey; Marc Schynts, Loncin; Jacques Delarge, Dolembreux, all of Belgium

[73] Assignee: Adir et Compagnie, Courbevoie, France

[21] Appl. No.: 474

[22] Filed: Jan. 5, 1993

[30] Foreign Application Priority Data

Jan. 6, 1992 [FR] France .................. 92 00031

[51] Int. Cl.⁶ .................. C07D 213/71; A61K 31/44
[52] U.S. Cl. .................. 514/347; 546/294
[58] Field of Search .................. 546/294; 514/347

[56] References Cited

PUBLICATIONS

Masereel et al., Journal of Pharmacy and Pharmacology, vol. 44, No. 7, pp. 589–593 Jul. 1992.

Primary Examiner—Alan L. Rotman
Attorney, Agent, or Firm—Gordon W. Hueschen

[57] ABSTRACT

The invention relates to the compound of formula (I)

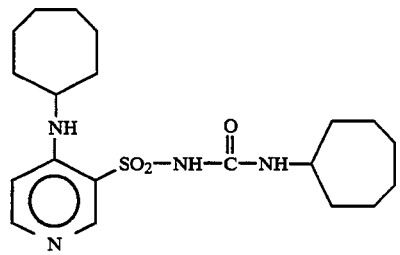

(I)

and the addition salts thereof with a pharmaceutically acceptable acid or base.

A pharmaceutical product which is useful for treating an ischemic or hypoxic disorder or a peripheral or central oedema.

6 Claims, No Drawings

NEW PYRIDYLSULPHONYLUREA COMPOUND

The invention relates to a new compound derived from pyridylsulphonylurea.

More specifically, the present invention relates to the compound of formula (I):

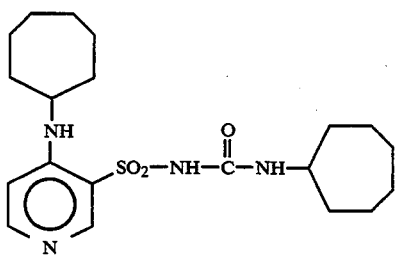

(I)

which is N-{[4-(cycloheptylamino)pyrid-3-yl]sulphonyl}-N'-(cycloheptyl)urea, and the addition salts thereof with a pharmaceutically acceptable acid or base.

Known from the prior art is European Patent Application 445 039 which claims compounds of the general formula (a)

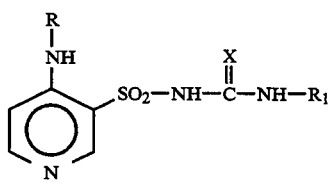

(a)

in which X may represent O or S,
R may represent a cycloalkyl radical optionally containing one or more hetero atoms,
and R1 may represent an alkyl radical, or a cycloalkyl radical optionally containing one or more hetero atoms,
those compounds being presented as anti-hypertensive agents and anti-oedematous agents. The compounds of European Patent Application 445 039 have proved to be powerful inhibitors of Na+/K+/2Cl-co-transport, the inhibition of that membrane transport constituting the mechanism of action of loop diuretics. They exhibit, especially, a distinct superiority over torasemide, one of the most powerful loop diuretics currently known. In addition, they permit, in a novel manner, a remarkable saving of potassium.

The compound of formula (I) is accordingly a particular case of the compounds of formula (a) wherein X is an oxygen atom, and where each of R and R1 represents a cycloheptyl radical. In no case, however, does this compound appear to the person skilled in the art, in the light of European Patent Application 445 039, to be of any particular value, because, although included in the scope of the general formula of claim 1, it is neither specifically described nor specifically claimed.

The Applicants have now discovered that the compound of the invention possesses surprising pharmacological activities.

The Applicants have discovered that the compound of the invention exhibits a very powerful and surprising anti-oedematous activity in comparison with the closest compound of the prior art.

The Applicants have also discovered that the compound of formula (I) inhibits the Cl- channel in a remarkable and very superior manner (by more than 50%) in comparison with the closest compounds of the prior art.

In addition, the Applicants have also discovered that the compound of the invention combines with its anti-oedematous activity a powerful anti-hypoxic and anti-ischaemic activity.

This activity was entirely unexpected because the prior art, and especially European Patent Application 445 039, neither mentions nor suggests such activity.

The toxicity of the compound of the invention has also been tested in the rat and in the mouse, it appears that the compound of the invention is particularly well tolerated since no mortality has been observed with doses superior to 3 200 mg/kg per os.

A process for the preparation of the compound of formula (I) is characterised in that: [4-(cycloheptylamino)pyrid-3-yl]sulphonamide of formula (II):

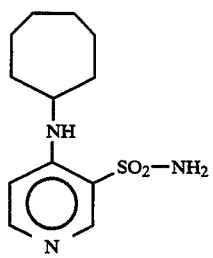

(II)

is reacted with a compound of formula (III):

$$Hal-CO-O-R_1$$ (III)

in which Hal represents a halogen atom and $R_1$ represents an alkyl radical having from 1 to 6 carbon atoms, to obtain a compound of formula (IV):

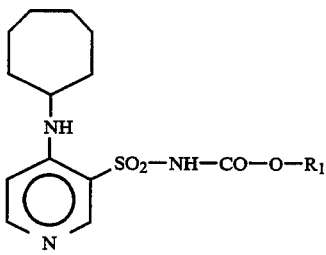

(IV)

in which $R_1$ is as defined above, which is then reacted with cycloheptylamine to yield the compound of formula (I) which, if desired, is purified and converted, where appropriate, into an addition salt thereof with a pharmaceutically acceptable acid or base.

A second process for the preparation of the compound of formula (I) is characterised in that: [4-(cycloheptylamino)pyrid-3-yl]sulphonamide of formula (II):

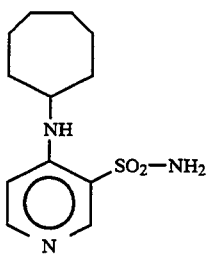

is reacted, in a polar solvent, with cycloheptyl isocyanate of formula (V)

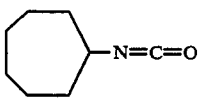

to yield the compound of formula (I) which, if desired, is purified and converted, where appropriate, into an addition salt thereof with a pharmaceutically acceptable acid or base.

The starting materials used in the processes described above are either commercially available or readily accessible to the person skilled in the art according to processes described in the literature, especially in European Patent Application 445 039.

Of the pharmaceutically acceptable acids that can be used to form an addition salt with the compound of the invention, there may be mentioned, by way of non-limiting examples, hydrochloric, sulphuric, phosphoric, tartaric, malic, maleic, fumaric, oxalic, methanesulphonic, ethanesulphonic, camphoric and citric acid.

Of the pharmaceutically acceptable bases that can be used to form an addition salt with the compound of the invention, there may be mentioned, by way of non-limiting examples, sodium, potassium, calcium and aluminium hydroxide, triethylamine, benzylamine, diethanolamine, tert-butylamine, dicyclohexylamine and arginine.

The Applicants have discovered that the compound of the invention exhibits a very valuable and surprising pharmacological activity compared with the closest compound of the prior art.

The compound of the invention exhibits a very powerful and surprising anti-oedematous activity (Example 3 of the present Application: Study of anti-oedematous activity in rabbits) compared with the compound of Example 8 of European Patent Application 445 039 (N-{[4-(cyclooctylamino)pyrid-3-yl]sulphonyl}-N'-(cycloheptyl)urea) which is structurally the closest compound of the prior art. In fact, the compound of that Example 8 differs only in the presence of an extra carbon-containing link in the cycloalkyl group in the 4-position of the pyridine ring.

In addition, the inhibitory activity of the compound of the invention on the Cl- channel (one of the factors involved in the uptake of cell water and accordingly in oedema) is also very superior to that of the compound of Example 8 of European Patent Application 445 039 (N-{[4-(cyclooctylamino)pyrid-3-yl]sulphonyl}-N'-(cycloheptyl)urea) which is structurally the closest compound of the prior art and which is also the compound that appears to be the most active in the inhibition of the Cl- channel (Example 19 of European Patent Application 445 039).

Furthermore, the Applicants have discovered that the compound of the invention also exhibits a remarkable and very powerful antiischaemic and anti-hypoxic activity.

The compound of the invention permits a surprising protection to be obtained, both in vitro and in vivo, against hypoxia (hypoxia test on astrocytes in culture and normobaric hypoxia test on mice, both described in our pharmacological study: Examples 5 and 6 of the present Application) and against ischaemia (test in respect of ischaemia induced in gerbils: Example 7 of the present Application).

Such an anti-hypoxic and anti-ischaemic activity of the compound of the invention is unexpected because European Patent Application 445 039 neither mentions nor suggests such properties in any case. This is confirmed by the pharmacological study (Examples 5, 6 and 7 of the present Application) on the compound of Example 8 of European Patent Application 445 039 (N-{[4-(cyclooctylamino)pyrid-3-yl]sulphonyl}-N'-(cycloheptyl)urea) which shows that this compound has no anti-hypoxic activity, even at higher doses, which reinforces the surprising aspect of the protective properties of the compound of the invention.

The remarkable pharmacological properties of the compound of the present invention make it especially valuable in the prevention and treatment of ischaemic and hypoxic disorders and peripheral and central oedemas. The compounds of the invention can accordingly be used in the treatment and prevention of cerebral ischaemia, cerebral vascular hypoxia, cerebral vascular anoxia, cerebral trauma, encephalopathies, neurovegetative diseases, post-ischaemic convulsions, and disorders connected with ageing, and also in the treatment and prevention of ischaemia of the peripheral type, and, in cardiology, in the treatment and prevention of myocardial ischaemia and coronary ischaemia and their various clinical manifestations: angina pectoris, myocardial infarct, rhythm disorders, vascular spasm, cardiac insufficiency, and also in ophthalmology and otorhinolaryngology during vascular chorio-retinitis episodes, vertigos of vascular origin, Menière's disease or vertigos of inner ear origin.

The invention extends also to pharmaceutical compositions containing as active ingredient the compound of formula (I) or one of the addition salts thereof, with a pharmaceutically acceptable acid or base, in combination with one or more pharmaceutically acceptable excipients.

Of the compositions according to the invention there may be mentioned by way of non-limiting examples those that are suitable for oral, parenteral, ocular, percutaneous, transcutaneous, nasal, rectal or perlingual administration or for administration by inhalation, and especially injectable preparations, aerosols, eye or nose drops, tablets, sublingual tablets, soft gelatin capsules, hard gelatin capsules, lozenges, glossettes, suppositories, creams, ointments and gels.

The preparations so obtained are generally presented in unit dose form and may contain, depending on the disorders being treated and the age and sex of the patient, from 0.01 to 100 mg of active ingredient (preferably from 0.01 to 10 mg, for example from 0.01 to 0.1 mg), to be administered from once to three times per day.

The following Examples illustrate the invention and do not limit it in any way.

EXAMPLE 1

N-{[4-(cycloheptylamino)pyrid-3-yl]sulphonyl}-N'-(cycloheptyl)urea

Stage A: N-{[4-(cycloheptylamino)pyrid-3-yl]sulphonyl}-N'-(ethoxycarbonyl)amine 3 g of [4-(cycloheptylamino)pyrid-3-yl]sulphonamide are suspended in 20 cm³ of anhydrous tetrahydrofuran, and one equivalent of triethylamine is added. The mixture is heated to 50° C. 10 cm³ of ethyl chloroformate are then added rapidly. A violent reflux results. Reflux and stirring are then maintained for 20 minutes.

The reaction mixture is filtered and the filtrate is evaporated under reduced pressure. The residue is then dissolved in a mixture of water and acetone (90/10) containing NaHCO₃.

After filtering, the pH of the filtrate is adjusted to 6.5. The N-{[4-(cycloheptylamino)pyrid-3-yl]sulphonyl}-N'-(ethoxycarbonyl) amine precipitated is suction-filtered and dried in vacuo.

Yield: 55%

Stage B: N-{[4-(cycloheptylamino)pyrid-3-yl]sulphonyl}-N'-(cycloheptyl) urea 3 g of the compound obtained in stage A are dissolved in 40 cm³ of anhydrous toluene and 2 cm3 of cycloheptylamine. 3 g of molecular sieve (0.4 nm) are also added.

The solution is heated to reflux and the progress of the reaction is monitored by thin layer chromatography.

At the end of the reaction, the toluene is evaporated in vacuo and the residue is taken up in a mixture of water and NaOH (90/10).

The excess amine in the alkaline solution is extracted with ether and then the aqueous phase is clarified with charcoal, filtered and adjusted to a pH of 6.5 with hydrochloric acid.

The N-{[4-(cycloheptylamino)pyrid-3-yl]sulphonyl}-N'-(cycloheptyl)urea so obtained is suction-filtered and then dried and may optionally be recrystallised from an aqueous alcoholic solution.

Yield: 64%

Melting point: 172°–174° C.

| % | Microanalysis: | | | |
|---|---|---|---|---|
| | C | H | N | S |
| calculated | 58.80 | 7.89 | 13.71 | 7.85 |
| found | 58.75 | 7.83 | 13.92 | 7.66 |

EXAMPLE 2

N-{[4-(cycloheptylamino)pyrid-3-yl]sulphonyl}-N'-(cycloheptyl)urea, second method 0.01 mol of NaOH in solution in a minimum of water is added to a solution of 2.4 g of (4-(cycloheptylamino)-pyrid-3-yl)sulphonamide in 80 cm³ of a mixture of water and acetone (1/1). Stirring is effected with a bar magnet and 2.1 g of cycloheptyl isocyanate are added. Stirring is continued while monitoring the progress of the reaction by thin layer chromatography. Evaporation is carried out in vacuo and the residue is taken up in 100 cm³ of 0.2N NaOH. After filtering, the pH of the solution is adjusted to 6.5 and the resulting precipitate is suction-filtered and then dried. The N-{[4-(cycloheptylamino)-pyrid-3-yl]sulphonyl}-N'-(cycloheptyl)urea so obtained may optionally be recrystallised from an aqueous alcoholic solution.

Yield: 68%

Melting point: 172°–174° C.

EXAMPLE 3

Study of anti-oedematous activity in rabbits in vivo

The oedema is induced in vivo by subjecting the animals to 30-minute periods of hypoxia by the bilateral occlusion of the common carotid arteries. Comparative analysis is then carried out at the frontal lobes on the control animals and the animals treated with the test compounds.

Protocol

In vivo study

The experiments are carried out on adult rabbits (Fauves de Bourgogne, weight: 2–2.5 kg). Seven animals are used for each experimental situation. Astrocyte swelling is induced by subjecting the animals' brains to 30-minute periods of hypoxia by bilateral occlusion of the common carotid arteries. Ultrastructural studies are carried out on samples removed from the frontal lobes of control rabbits, hypoxiated rabbits, and treated hypoxiated rabbits.

The animals, pre-anaesthetised with chlorpromazine (65 mg/kg) and anaesthetised with pentobarbitone sodium (20 mg/kg) receive the test compound by injection into the marginal vein of the ear 10 minutes before the commencement of hypoxia. The initial dose of the test compound is 10 mg/kg.

At the end of the period of hypoxia, the animals are sacrificed by intracardiac perfusion of the fixing solution (2.5% glutaraldehyde in 0.1M phosphate buffer, pH 7.4).

The samples taken continue to be fixed in the same fixing agent for 1 hour and are then washed with 0.1M phosphate buffer to which 0.18M saccharose has been added and are then treated with 1% osmium tetroxide in phosphate buffer, then dehydrated, enclosed and cut on an ultratome with a diamond blade, after which the sections, mounted on grids, are observed under an electron microscope.

Results

Ultrastructural analysis of the sections under an electron microscope establishes the presence in the hypoxiated animals of a characteristic cerebral oedema (swelling of the astrocytes, deterioration of the nuclei and mitochondria).

The compound of the invention is found to exhibit a powerful anti-oedematous activity because the cerebral sections taken from animals pretreated with 10 mg/kg of the compound of the invention do not reveal any oedema.

On the other hand, at that same dose of 10 mg/kg, the compound of Example 8 of European Patent Application 445 039, the compound of the prior art that is the closest structurally, provides only weak anti-oedematous protection.

EXAMPLE 4

Study of the inhibitory activity on the Cl- channel

This study makes it possible to determine the concentration of the compounds inhibiting the Cl- channel by 50% ($IC_{50}$). This test was carried out on the Cl- channel present on the basolateral membrane of the ascending branch of the loop of Henlé of the perfused rabbit kidney, and the degree of inhibition is determined by electrophysiology.

The compound of the invention was compared with torasemide which is one of the most powerful diuretics currently known that act on the ascending branch of the loop of Henlé.

It is also compared with the compound of Example 8 of European Patent Application 445 039 (N-{[4-(cyclooctylamino)pyrid-3-yl]sulphonyl}-N'-cycloheptylurea).

The results surprisingly demonstrate the superiority of the compound of the invention in the inhibition of the Cl- channel because its $IC_{50}$, that is to say, the concentration that is necessary for 50% inhibition, is 80% lower than that of torasemide and more than 50% lower than that of Example 8 of European Patent Application 445 039, which is the closest compound of the prior art.

EXAMPLE 5

Study of anti-hypoxic activity in vitro

Astrocytes in culture constitute a preferred model for the detection of cytoprotective activity in conditions of hypoxia.

The first visible cellular reaction to any cerebral damage is a deterioration of astrocytic integrity, even though the neurones, the oligodendrocytes and the endothelial cells still have a normal morphological profile.

In addition, it has been demonstrated that astrocytes play a major role in the brain, especially in the elaboration of neurotransmitter amino acids and in the maintenance of extracellular ionic equilibrium.

The Applicants therefore tested the effect of the compound of the invention on the cellular protection of astrocytes in culture and placed in conditions of hypoxia, by analysing an enzymatic marker (lactate dehydrogenase or LDH) which permits the cellular lysis of the astrocytes to be measured.

Methodology

Rat astrocytes in a primary culture are prepared from cortex originating from the brains of new-born rats. The hypoxic treatment consists in exposing the cells, in a humid atmosphere, to a mixture of gases consisting of 95% $N_2$ and 5% $CO_2$, at 37° C. for 15 hours.

The test compounds are added to the culture medium 12 hours before hypoxia. A second addition is carried out at the end of the period of hypoxia. Two hours after the end of the hypoxia, the extracellular lactate dehydrogenase activity is measured by spectrophotometric analysis at 340 nm on the culture medium.

Results

The compound of the invention exhibits an exceptional antihypoxic activity because it permits the avoidance of cellular lysis, which would normally be caused by hypoxia and is measured in the control experiment without a product.

This result is surprising because neither furosemide nor one of the closest compounds of the prior art (Example 8 of European Patent Application 445 039 , which is N-{[4-(cyclooctylamino)pyrid-3-yl]sulphonyl}-N'-(cycloheptyl)urea exhibits any action on this cellular lysis.

By way of example, a comparison between the compound of the invention and furosemide after a period of 18 hours of hypoxia demonstrates that, at a concentration of 10 $\mu$M, the compound of the invention results in nearly 90% astrocyte protection while furosemide, at the same concentration, exhibits no protective activity.

These results demonstrate the value of the compound of the invention in the treatment of cerebral hypoxic trauma and associated pathologies.

EXAMPLE 6

Study of anti-hypoxic activity in vivo

Animals (mice) are placed in an atmosphere low in oxygen, which brings about the occurrence of suffocation.

The compounds exhibiting anti-hypoxic properties induce a delay in the occurrence of suffocation.

The Applicants have now tested the compound of the invention in this test.

Methodology

Male mice (Swiss CD1) weighing from 25 to 30 g are housed for 1 week before any experiment under normal animal house conditions (20°–22° C., 55% humidity, 12/12 light/darkness cycle, commercial feed and water as desired).

The mice are placed in a box (7×5×5 cm) in which an atmosphere low in oxygen is created by the passage of air consisting of 96% $N_2$ and 4%

The period before the occurrence of the first suffocations is measured. The mice receive a dose of the test compounds intraperitoneally.

Results

The compound of the invention exhibits a significant anti-hypoxic activity at a dose of 0.1 mg/kg and above while the closest compound of the prior art (Example 8 of European Patent Application 445 039, N-{[4-(cyclooctylamino)pyrid-3-yl]sulphonyl}-N'-(cycloheptyl)urea exhibits no anti-hypoxic activity even at a dose of 20 mg/kg, that is to say, a dose 200 times larger.

EXAMPLE 7

Detection of anti-ischaemic activity in vivo

Some gerbils (from 40 to 60% of cases), referred to as sensitive, exhibit a Willis' circle anomaly (Levine et al. Exp. Neurol. 1966; 16: 255–262).

Because of that anomaly, the occlusion of a carotid artery in gerbils makes it possible, unlike the case of other animal species, to reproduce the pathology of human ischaemia.

The Applicants therefore tested the influence of the compound of the invention on the survival of gerbils that had undergone cerebral ischaemia as a result of ligation of the left carotid artery.

Methodology

The "sensitive" gerbils are anaesthetised intraperitoneally with Kétalar ® at a dose of 60 mg/kg and, 30 minutes before ligation of the left carotid artery, various concentrations of the compound of the invention in solution in the presence of 10% gum arabic and in a volume of 0.1 $cm^3$ are administered orally.

The response of the animals is analysed at various times.

Results

The compound of the invention exhibits a very powerful antiischaemic protective activity.

At 96 hours, while all the animals in the control experiment are dead, the compound of the invention, administered per os, makes it possible, at a dose of 0.1 mg/kg and above, to obtain a high percentage survival rate (83% at 0.1 mg/kg, which is a much greater activity than that of the closest compound of the prior art (Example 8 of European Patent Application 445 039)).

In addition, the study carried out on the treated animals demonstrates that the compound of the invention permits, up to 96 hours, a significant protection. The compound of the invention exhibits, especially, an activity that strongly inhibits postischaemic convulsions.

EXAMPLE 8

Pharmaceutical composition

Tablets containing 1 mg of N-{[4-(cycloheptylamino)pyrid-3-yl]sulphonyl}-N'-(cycloheptyl)urea

| | |
|---|---|
| Formula for 1000 tablets N-{[4-(cycloheptylamino)pyrid-3-yl]sulphonyl}-N'-(cycloheptyl)urea | 1 g |
| lactose | 15 g |
| corn starch | 50 g |
| colloidal silica | 0.2 g |
| magnesium stearate | 0.1 g |

We claim:

1. A compound selected from those having formula (I)

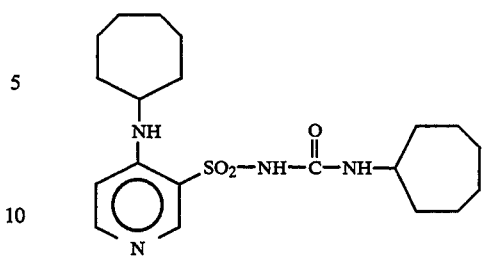

which is N-{[4-(cycloheptylamino)pyrid-3-yl]sulphonyl}-N'-(cycloheptyl)urea and the addition salts thereof with a pharmaceutically acceptable acid or base.

2. A pharmaceutical composition containing as active ingredient a compound according to claim 1 in combination with a pharmaceutically-acceptable carrier or diluent.

3. A method for treating a mammal afflicted with a disorder selected from an ischemic or hypoxic disorder and periperipheral or central oedema comprising the step of administering to the said mammal an amount of a compound of the claim 1 which is effective for alleviation of said disorder.

4. A method for treating a mammal afflicted with an ischemic or hypoxic disorder comprising the step of administering to the said mammal an amount of a compound of claim 1 which is effective for alleviation of said disorder.

5. A method of claim 3 wherein the compound is administered in the form of a pharmaceutical composition comprising a pharmaceutically-acceptable carrier or diluent.

6. A method of claim 4 wherein the compound is administered in the form of a pharmaceutical composition comprising a pharmaceutically-acceptable carrier or diluent.

* * * * *

UNITED STATES PATENT AND TRADEMARK OFFICE
CERTIFICATE OF CORRECTION

PATENT NO. : 5,391,559             Page 1 of 2
DATED : February 21, 1995
INVENTOR(S) : Bernard Masereel, Bernard Pirotte, Marc Schynts and Jacques Delarge It is certified that error appears in the above-indentified patent and that said Letters Patent is hereby corrected as shown below:

Title Page, item [21], Appl. No.; "474" should read -- 000,474 -- (filing receipt)
Col. 1, line 46; insert a space between "2Cl-" and "co-transport,"
Col. 4, line 3; "antiischaemic" should read -- anti-ischaemic --
Col. 6, line 12; "Protocol" should read -- Protocol: --
Col. 6, line 41; "Results" should read -- Results: --
Col. 7, line 36; "Methodology" should read -- Methodology: --
Col. 7, line 48; "Results" should read -- Results: --
Col. 8, line 11; "Methodology" should read -- Methodology: --
Col. 8, line 19; "and 4%" should read -- and 4% $O_2$. --
Col. 8, line 23; "Results" should read -- Results: --
Col. 8, line 45; "Methodology" should read -- Methodology: --
Col. 8, line 54; "Results" should read -- Results: --
Col. 8, line 56; "antiischaemic" should read -- anti-ischaemic --
Col. 8, line 68; "postischaemic" should read -- post-ischaemic --
Col. 10, line 14; "urea" should read -- urea, --

UNITED STATES PATENT AND TRADEMARK OFFICE
CERTIFICATE OF CORRECTION

PATENT NO. : 5,391,559  
DATED : February 21, 1995  
INVENTOR(S) : Bernard Masereel, Bernard Pirotte, Marc Schynts and Jacques Delarge It is certified that error appears in the above-indentified patent and that said Letters Patent is hereby corrected as shown below:

Col. 10, line 14; "and the" should read -- and an --

Col. 10, line 14; "salts" should read -- salt --

Col. 10, line 15; "pharmaceutically acceptable" should read -- pharmaceutically-acceptable --

Signed and Sealed this

Eighteenth Day of July, 1995

*Attest:*

BRUCE LEHMAN

*Attesting Officer*   *Commissioner of Patents and Trademarks*